(12) United States Patent  
Ikegami (10) Patent No.: US 8,931,901 B2  
(45) Date of Patent: Jan. 13, 2015

(54) OPHTHALMOLOGIC APPARATUS

(71) Applicant: Canon Kabushiki Kaisha, Tokyo (JP)

(72) Inventor: Tomoyuki Ikegami, Hiratsuka (JP)

(73) Assignee: Canon Kabushiki Kaisha, Toyko (JP)

( * ) Notice: Subject to any disclaimer, the term of this patent is extended or adjusted under 35 U.S.C. 154(b) by 0 days.

(21) Appl. No.: 14/055,187

(22) Filed: Oct. 16, 2013

(65) Prior Publication Data

US 2014/0111772 A1 Apr. 24, 2014

(30) Foreign Application Priority Data

Oct. 18, 2012 (JP) ................................. 2012-231020

(51) Int. Cl.  
*A61B 3/10* (2006.01)  
*A61B 3/14* (2006.01)

(52) U.S. Cl.  
USPC ............................ 351/211; 351/206; 351/205

(58) Field of Classification Search  
USPC ............................................... 351/200–246  
See application file for complete search history.

(56) References Cited

U.S. PATENT DOCUMENTS 7,290,881 B2* 11/2007 Matsumoto ................... 351/214  
2007/0291344 A1* 12/2007 Yamauchi et al. ............ 359/205  
2011/0273538 A1* 11/2011 Suzuki ............................ 348/49

FOREIGN PATENT DOCUMENTS

JP 3927873 B2 6/2007

* cited by examiner

*Primary Examiner* — Mohammed Hasan  
(74) *Attorney, Agent, or Firm* — Canon USA Inc. IP Division (57) ABSTRACT

An ophthalmologic apparatus includes a projection optical system configured to project a light flux on a subject's eye, a beam splitting member configured to form a split optical path corresponding to a light flux from a subject's eye, and an image-forming optical system configured to receive via the beam splitting member a light flux from the subject's eye, the image-forming optical system including an optical element having an optical characteristic that reduces astigmatism generated by the beam splitting member.

20 Claims, 11 Drawing Sheets

OPHTHALMOLOGIC APPARATUS

BACKGROUND OF THE INVENTION

1. Field of the Invention

The present invention relates to an ophthalmologic apparatus which obtains unique information on a subject's eye (e.g., eye refractive power, a cornea shape, and a fundus image) or alignment information.

2. Description of the Related Art

An eye refractive power measuring apparatus is conventionally known as an ophthalmologic apparatus, which projects an index on a fundus of a subject's eye and then measures spherical refractive power, astigmatic refractive power, and an astigmatic axial angle of the subject's eye based on the reflected fundus image. In general, the eye refractive power measuring apparatus projects an index on a fundus of a subject's eye, forms and detects reflected light from the fundus as a ring image on a two-dimensional sensor therein, and then calculates and outputs a radius of the ring image as the spherical refractive power, and distortion of the ring image as the astigmatic refractive power.

In recent years, optical systems in the eye refractive power measuring apparatus have become complex along with downsizing of the apparatus. It has become common that a plurality of optical systems is combined or divided and the optical system on the exit side of an objective lens on the subject side is shared in the apparatus.

Examples of a plurality of optical systems in the eye refractive power measuring apparatus, other than an eye refractive power measuring optical system are as follows. An anterior eye observation optical system is used for selecting and confirming a measurement range. An alignment optical system is used for aligning the apparatus and a subject's eye. A fixation target optical system guides fixation and focusing state of a subject's eye by using an index in the apparatus. Further, there is a cornea shape measuring optical system for measuring a cornea shape, depending on the product configuration.

The ophthalmologic apparatus discussed in Japanese Patent No. 3927873 includes a dichroic mirror which is arranged near the exit side of an objective lens and used as a beam splitting member in a light receiving system and as a beam combining member in a light projecting system. The dichroic mirror transmits a wavelength used for a transmission optical system and reflects a wavelength used for a reflection optical system, and the optical system on the exit side of an objective lens is shared in the apparatus. An eye refractive power measuring optical system is used as the transmission optical system. An observation optical system, a fixation target optical system, and a cornea shape measuring optical system are used as the reflection optical system.

The dichroic mirror which is employed for transmitting or reflecting a wavelength is generally a parallel plate glass having a thickness of several millimeters. The dichroic mirror is arranged to be tilted by approximately 45 degrees with respect to an optical axis in a measurement optical path (i.e., an optical path of a light receiving system which receives reflected light from a fundus).

SUMMARY OF THE INVENTION

The present invention is directed to an ophthalmologic apparatus which reduces astigmatism generated by a beam splitting member such as a dichroic mirror in a light receiving system.

According to an aspect of the present invention, an ophthalmologic apparatus includes a projection optical system configured to project a light flux on a subject's eye, a beam splitting member configured to form a split optical path corresponding to a light flux from the subject's eye, and an image-forming optical system configured to receive a light flux from the subject's eye via the beam splitting member, the image-forming optical system including an optical element having an optical characteristic that reduces astigmatism generated by the beam splitting member.

Further features of the present invention will become apparent from the following description of exemplary embodiments with reference to the attached drawings.

DESCRIPTION OF THE EMBODIMENTS

Various exemplary embodiments, features, and aspects of the invention will be described in detail below with reference to the drawings.

Figure 3A:
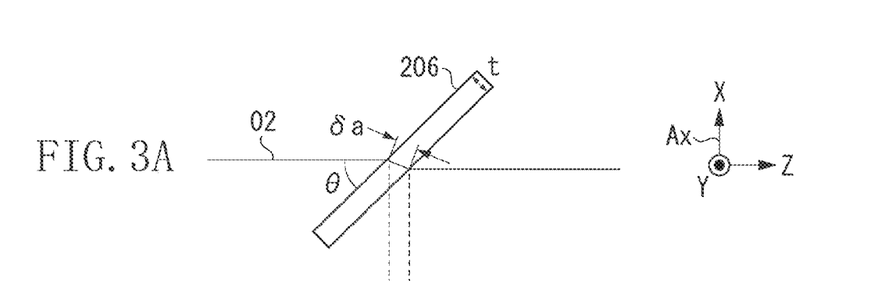
FIGS. 3A and 3B relate to astigmatism caused by a dichroic mirror according to an exemplary embodiment of the present invention, respectively illustrating a principal ray optical path of reflected light from a fundus in a vertical direction (i.e., x direction), and a principal ray optical path of reflected light from a fundus in a horizontal direction (i.e., y direction).
Figure 3B:
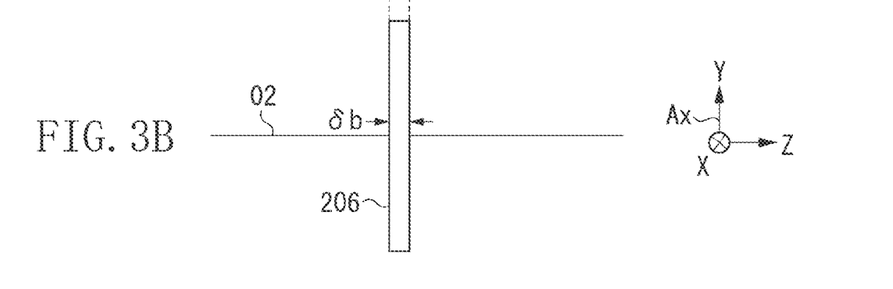

Astigmatism is generated by arranging a dichroic mirror at an inclination of approximately 45 degrees with respect to an optical axis (refer to FIGS. 3A and 3B). More specifically, when a dichroic mirror is tilted with respect to the optical axis in an X-Z plane, the focal length in the X-Z plane is longer than the focal length in a Y-Z plane. A difference of image-forming position occurs between the X-Z plane and the Y-Z plane. As a result, astigmatism is generated. The state (e.g., shape) of a ring image in an eye refractive power measurement changes due to the generated astigmatism (refer to FIG. 4B).

According to the present exemplary embodiment, an optical element having an optical characteristic that reduces the astigmatism generated by a dichroic mirror, an example of a beam splitting member, is arranged in a light receiving system. As a result, the astigmatism generated by a beam splitting member such as a dichroic mirror can be reduced.

Figure 2:
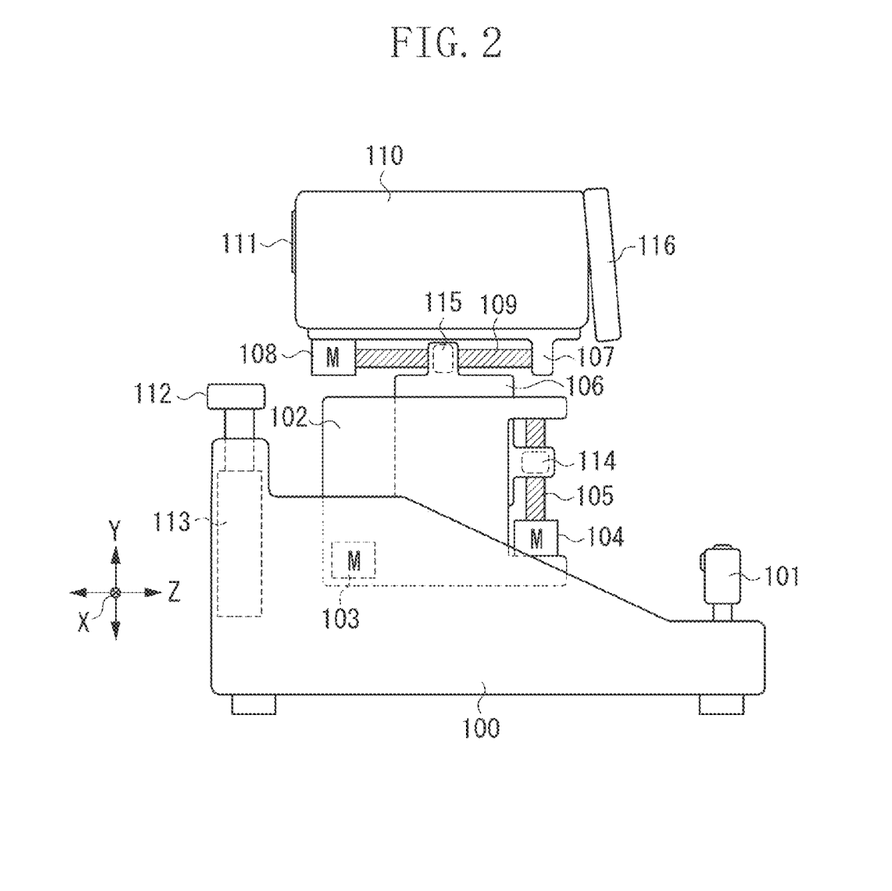
FIG. 2 is an external view illustrating the eye refractive power measuring apparatus according to an exemplary embodiment of the present invention.

FIG. 2 is a schematic diagram illustrating a configuration of an eye refractive power measuring apparatus, which is an ophthalmologic apparatus according to a first exemplary embodiment of the present invention. A frame 102 is movable in the horizontal direction (hereinafter referred to as the X-axis direction) with respect to a base 100. A driving mechanism in the X-axis direction includes an X-axis drive motor 103 fixed on the base 100, a feed screw (not illustrated) connected to a motor output shaft, and a nut (not illustrated) fixed to the frame 102 to be movable in the X-axis direction on the feed screw. The frame 102 moves via the feed screw and the nut in the X-axis direction by rotation of the motor 103.

A frame 106 is movable in the vertical direction (hereinafter referred to as the Y-axis direction) with respect to the frame 102. A driving mechanism in the Y-axis direction includes an Y-axis drive motor 104 fixed on the frame 102, a feed screw 105 connected to a motor output shaft, and a nut 114 fixed to the frame 106 to be movable in the Y-axis direction on the feed screw 105. The frame 106 moves via the feed screw 105 and the nut 114 in the Y-axis direction by rotation of the motor 104.

A frame 107 is movable in the forward/backward direction (hereinafter referred to as the Z-axis direction) with respect to the frame 106. A driving mechanism in the Z-axis direction includes a Z-axis drive motor 108 fixed on the frame 107, a feed screw 109 connected to a motor output shaft, and a nut 115 fixed to the frame 106 to be movable in the Z-axis direction on the feed screw 109.

The frame 107 moves via the feed screw 109 and the nut 115 in the Z-axis direction by rotation of the motor 108. A measurement unit 110, which measures eye refractive power as a unique information acquisition unit, is fixed on the frame 107.

A light source (not illustrated) used for performing alignment and a light source unit 111 for measuring a corneal curvature are disposed on the subject side end of the measurement unit 110.

Further, a joystick 101 which is an operation member for aligning the measurement unit 110 with a subject's eye is disposed on the frame 100. To perform alignment, the operator tilts the joystick 101 in the horizontal direction (i.e., the x direction) and the forward/backward direction (i.e., the z direction) to make a position adjustment in the respective directions. Further, the operator rotates the joystick 101 to make a position adjustment in the vertical direction (i.e., the y direction).

When refractive power is to be measured, a subject places the chin on a chin rest 112 and presses the forehead against a forehead supporting portion of a face supporting frame (not illustrated) fixed on the frame 100. The position of the subject's eye can thus be fixed. Further, a chin rest drive mechanism 113 can adjust the chin rest 112 in the Y-axis direction according to the size of the subject's face.

A liquid crystal display (LCD) monitor 116 which is a display member for observing a subject's eye is disposed on the operator side end of the measurement unit 110. The LCD monitor 116 can display measurement results.

Figure 1:
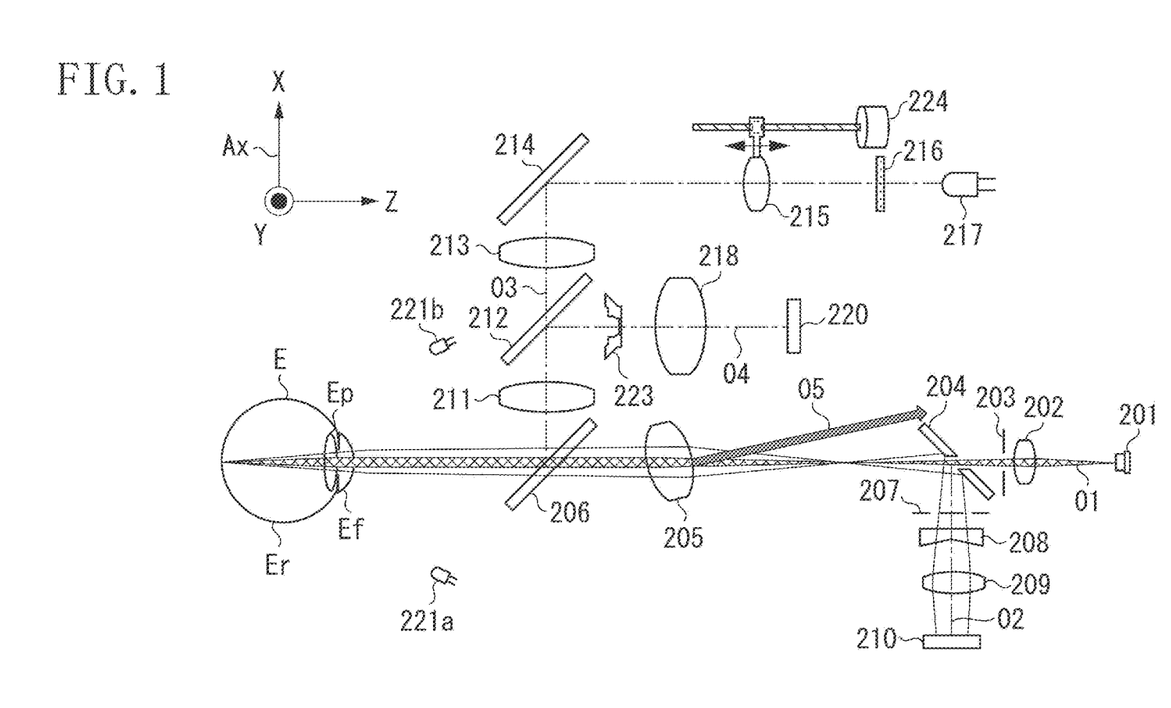
FIG. 1 illustrates a configuration of an optical system in a measurement unit of an eye refractive power measuring apparatus according to an exemplary embodiment of the present invention.

FIG. 1 illustrates a schematic diagram illustrating optical systems in the measurement unit 110. Referring to FIG. 1, an optical path 01 of a first optical system leads from an eye refractive power measurement light source 201 to a subject's eye E. A lens 202, a diaphragm 203 which is substantially conjugate with a pupil Ep of a subject's eye E, a perforated mirror 204, and a lens 205 are sequentially arranged on the optical path 01 so that an index light flux can be irradiated on a fundus of the subject's eye by using an irradiation light flux of 880 nm wavelength. Further, a dichroic mirror 206 is arranged on the light path 01 to totally reflect the infrared light and visible light having a wavelength of less than 880 nm and partially reflect the light flux having a wavelength of 880 nm or longer, from the subject's eye E side.

A ring diaphragm 207, a light flux splitting prism 208, a lens 209, and an image sensor 210 are sequentially arranged on a light path 02 in a reflection direction of the perforated mirror 204. The ring diaphragm 207 is substantially conjugate with the pupil Ep, and has a ring-shaped slit. The above-described optical system is used for measuring eye refractive power. A light flux emitted from the measurement light source 201 is narrowed by the diaphragm 203, and primarily imaged in front of the objective lens 205 by the lens 202. The light flux is then transmitted through the objective lens 205 and the dichroic mirror 206, and projected on a center of the pupil of the subject's eye E.

A fundus Er of the subject's eye reflects the projected light flux, so that the reflected light passes through a peripheral portion of the pupil and again becomes incident on the objective lens 205. The incident light flux passes through the objective lens 205, and is reflected by the peripheral portion of the perforated mirror 204. The reflected light flux is then pupil-split by the ring diaphragm 207, which is substantially conjugate with the pupil Ep of the subject's eye, and the light flux splitting prism 208, and is projected as a ring image on a light receiving surface of the image sensor 210 via a second optical system including the objective lens 205.

If the subject's eye E is an emmetropic eye, the output ring-shaped image has a predetermined circle. If the subject's eye E is a short-sighted eye, the output ring-shaped image has a smaller circle than that of the emmetropic eye. Further, if the subject's eye E is a far-sighted eye, the output ring-shaped image has a larger circle than that of the emmetropic eye. Furthermore, if the subject's eye E is astigmatic, the output ring-shaped image has an ellipse. An angle formed by the horizontal axis and the ellipse is considered as the astigmatic axial angle. Eye refractive power information is obtained based on the output ring-shaped image.

A fixation target projection optical system and an alignment light receiving optical system are arranged in the reflection direction of the dichroic mirror 206. The alignment light receiving optical system is used for both observing an anterior eye portion of a subject's eye and detecting alignment.

A lens 211, a dichroic mirror 212, a lens 213, a reflecting mirror 214, a lens 215, a fixation target 216, and a fixation target illumination light source 217 are sequentially arranged on a light path 03 of the fixation target projection optical system.

When the measurement unit 110 is to perform fixation guiding, the fixation target illumination light source 217 is turned on, and a projection light flux from the fixation target illumination light source 217 illuminates the fixation target 216 from a rear side. The projection light flux is then projected on the fundus Er of the subject's eye E via the lens 215, the reflecting mirror 214, the lens 213, the dichroic mirror 212, and the lens 211.

A fixation guiding motor 224 can move the lens 215 in the optical axis direction to realize a fogged state by performing diopter guiding of the subject's eye E.

The eye refractive power measurement light source 201 is used as a first irradiation unit, i.e., a light source for performing alignment detection. When performing alignment, a diffusion plate insertion and removal solenoid (not illustrated) inserts a translucent diffusion plate in a proximate focus position of the objective lens 205. As a result, the image of the measurement light source 201 is once projected on the diffusion plate, becomes a secondary light source, and is projected from the objective lens 205 towards the subject's eye E as a thick parallel light flux (the first irradiation unit).

The parallel light flux is reflected by a cornea Ef of the subject's eye, and then forms a luminescent spot image (i.e., a virtual image) on a cornea focus position. Part of the cornea reflected light flux is reflected by the dichroic mirror 206 again, and then reflected by the dichroic mirror 212 via the lens 211. The reflected light flux passes through a center aperture of an alignment prism diaphragm 223, and alignment prisms and apertures at both ends thereof. The light flux is converged by a lens 218 and formed into three index images on an image sensor 220.

In addition to the first irradiation unit which irradiates a subject's eye E with a parallel light flux, anterior eye illumination light sources 221a and 221b (i.e., a second irradiation unit), which irradiate an anterior eye portion with light of approximately 780 nm wavelength, are arranged diagonally in front of the anterior eye portion of the subject's eye E. An image of the anterior eye portion of the subject's eye E irradiated by the anterior eye portion illumination light sources 221a and 221b is formed on a light receiving sensor surface of the image sensor 220 via the dichroic mirror 206, the lens 211, the dichroic mirror 212, and the center aperture of the alignment prism diaphragm 223.

The center aperture of the alignment prism diaphragm 223 transmits the light flux having a wavelength of 780 nm or longer, emitted from the anterior eye illumination light sources 221a and 221b. After an anterior eye portion is illuminated by the anterior eye illumination light sources 221a and 221b, the light flux reflected by the anterior eye portion travels along the observation optical system. This is similar to the path of the light flux reflected by the cornea Ef. The light flux reflected by the anterior eye portion passes through the center aperture of the alignment prism diaphragm 223 and then is imaged on the image sensor 220 by the imaging lens 218. In other words, the image of the anterior eye portion, including an iris and the image formed by a cornea reflected light flux from the illumination light sources 221a and 221b, is formed on the image sensor 220.

Alignment control is performed in the horizontal direction and the vertical direction so that a center index image among the three index images obtained via the alignment prism diaphragm 223 is at the center of the pupil. Further, alignment control is performed in the forward/backward direction so that the three index images are aligned in the vertical direction (i.e., the perpendicular direction). The alignment prisms disposed corresponding to the apertures at both ends of the alignment prism diaphragm 223 transmit light fluxes. The prisms cause the light fluxes to be refracted and displaced in opposite directions of each other.

Upon detection of the three index images, a system control unit (not illustrated) controls a motor drive circuit (not illustrated), and drives the measurement unit 110 in the vertical and horizontal directions so that the center index image matches a central direction. The system control unit then drives the measurement unit 110 in the forward/backward direction so that the two index images at both ends are aligned in the vertical direction (i.e., the perpendicular direction) with respect to the center index image. When the three index images are aligned in a line in the vertical direction (i.e., the perpendicular direction), alignment is completed.

The astigmatism generated by tilting the dichroic mirror 206 will be described below with reference to FIGS. 3A and 3B. FIGS. 3A and 3B illustrate the dichroic mirror 206 arranged to be tilted and the principal ray optical path of the fundus reflected light 02. FIGS. 3A and 3B also illustrate the X-Z plane and the Y-Z plane in an optical system, respectively. Further, FIG. 3B illustrates the state in which the dichroic mirror 206 is transmitting the light. The dichroic mirror 206 has a thickness of t and is arranged to be tilted by $\theta$ degrees with respect to the Y axis as a rotational axis. The light flux projected on a fundus is diffusely and isotropically reflected in all directions.

However, if the dichroic mirror 206 is highly tilted by approximately 45 degrees as in the arrangement herein, the optical system is anisotropic. In FIGS. 3A and 3B, it is assumed that a refractive index of glass is n, and the optical path length in the X-Z plane n×$\delta$a and the optical path length in the Y-Z plane n×$\delta$b are compared to each other. The X-Z plane in which the dichroic mirror 206 is tilted is affected by refraction at the surface of the dichroic mirror 206, and the optical path length in the glass is relatively longer. As a result, the focal length is longer in the X-Z plane than in the Y-Z plane in the optical system. A difference in image forming position occurs between the X-Z plane and the Y-Z plane. As a result, astigmatism is generated.

Figure 4A:
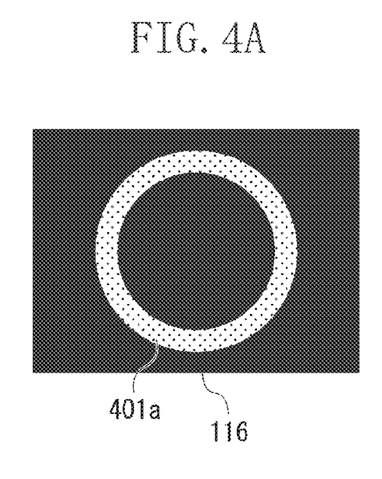
FIGS. 4A and 4B relate to influence of astigmatism on a ring image according to an exemplary embodiment of the present invention, respectively illustrating a ring image generated by a non-astigmatic optical system, and a ring image generated by an astigmatic optical system.
Figure 4B:
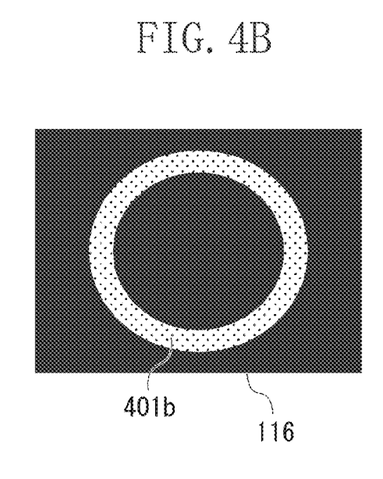

FIGS. 4A and 4B illustrate examples of a ring image which is imaged by the image sensor 210 in the optical system of the eye refractive power measuring apparatus and displayed on the LCD monitor 116. As described above, refractive power of a subject's eye is obtained based on the ring image. In the examples illustrated in FIGS. 4A and 4B, the subject's eye is an emmetropic eye which is non-astigmatic. FIG. 4A illustrates a ring image 401a obtained by a non-astigmatic optical system, and FIG. 4B illustrates a ring image 401b obtained by an astigmatic optical system. If the optical system is non-astigmatic (as illustrated in FIG. 4A), the ring image 401a is detected as an almost exact circle.

On the other hand, if the optical system is highly astigmatic (as illustrated in FIG. 4B), there is a difference in the focal length of the optical system between the vertical direction and the horizontal direction. The ring image 401b is thus formed as an ellipse. Astigmatic refractive power is calculated and output based on the aspect ratio of the ellipse. As a result, astigmatic refractive power is added in an output measurement value even when the subject's eye is emmetropic and not astigmatic. The astigmatism generated by tilting the dichroic mirror 206 thus affects measurement accuracy of the eye refractive power measuring apparatus. As described above, a simple arrangement of the dichroic mirror causes a problem in the quality of the apparatus. A method for correcting and improving the astigmatism will be described below.

Figure 5:
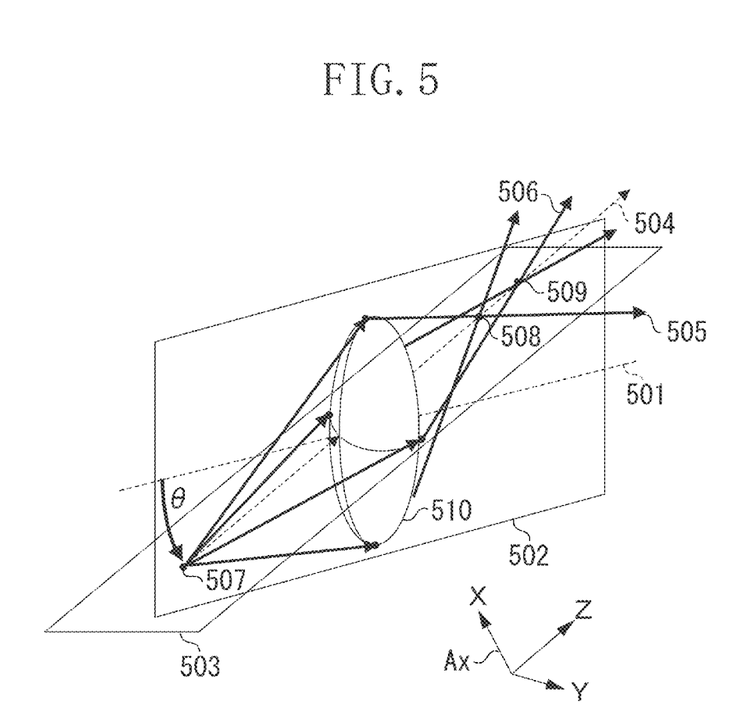
FIG. 5 illustrates astigmatism generated by tilting an objective lens according to an exemplary embodiment of the present invention.

FIG. 5 qualitatively illustrates how astigmatism is generated when a lens is tilted with respect to an optical axis. Referring to FIG. 5, an object point 507 is incident on a lens 510 at a viewing angle $\theta$ with respect to an optical axis 501 of the lens 510. Planes 502 and 503 respectively correspond to the X-Z plane and the Y-Z plane in the optical system of the apparatus. A principal ray 504 from the object point 507 passes through the center of the lens 510, and marginal rays 505 and 506 are respectively in the X-Z plane 502 and the Y-Z plane 503. The object point 507 having the viewing angle θ with respect to the optical axis 501 is synonymous with the lens 510 rotating by θ degrees around the Y axis in the X-Z plane 502.

In the example illustrated in FIG. 5, the X-Z plane 502 is a meridional plane which passes through the optical axis of the lens 510 and the object point 507. Further, the Y-Z plane 503 is a sagittal plane which is perpendicular to the X-Z plane 502 and passes through the object point 507. The power of the meridional plane is characteristically stronger than the power of the sagittal plane in terms of astigmatism. Thus, the focal length in the Y-Z plane 503 is longer than that in the X-Z plane 502. An image is formed on the principal ray 504 at different positions in the X-Z plane 502 and the Y-Z plane 503, i.e., at an X image position 508 and a Y image position 509. As described above, astigmatism is also generated in the case where the lens is tilted with respect to the optical system of the apparatus. Combination of the astigmatism generated by the dichroic mirror and the astigmatism generated by tilting the lens will be described below.

Figure 6:
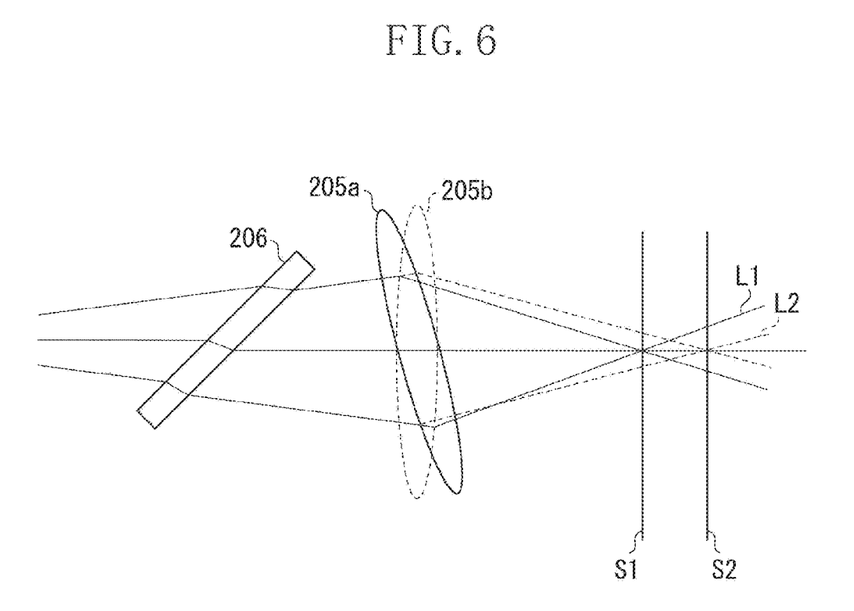
FIG. 6 illustrates the astigmatism generated by the dichroic mirror and the astigmatism generated by tilting the objective lens cancelling each other according to an exemplary embodiment of the present invention.

FIG. 6 illustrates the dichroic mirror 206, and the position and optical path of the objective lens 205 in the X-Z plane of the optical system according to the two conditions below. Condition 1 is that an objective lens 205a is arranged to be tilted with respect to the optical system of the apparatus and an optical path L1 is formed into an image at a primary image-forming plane S1. Condition 2 is that an objective lens 205b is arranged to be perpendicular with respect to the optical system of the apparatus as in a conventional manner and an optical path L2 is formed into an image at a primary image-forming plane S2. Conditions 1 and 2 have the same object point. The primary image-forming plane S1 is the same as the primary image-forming plane in the Y-Z plane (not illustrated).

The primary image-forming plane in the Y-Z plane does not change between conditions 1 and 2. As in condition 2, if the objective lens 205b is perpendicularly arranged as in a conventional manner, the light path L2 is affected by the astigmatism generated by the dichroic mirror 206, and the primary image-forming plane S2 is positioned farther back than the primary image-forming plane in the Y-Z plane.

On the other hand, if the objective lens 205a is arranged to be tilted as in condition 1, the influence of the astigmatism due to the dichroic mirror 206 and the influence of the astigmatism due to the tilted objective lens 205a cancel each other. As a result, the astigmatism is corrected. The light path L1 is thus formed into an image at the same position as the primary image-forming plane in the Y-Z plane. The method for correcting the astigmatism is as described above.

A cylindrical lens may be added in the light path as a method for reducing the astigmatism within the scope of the exemplary embodiments of the present invention. However, the present exemplary embodiment is advantageous in view of light amount and cost because an additional optical surface is not required in the eye refractive power optical system which detects an extremely low amount of fundus-reflected light. Further, a dichroic prism having a thin reflective surface within a cubic prism may be used to reduce astigmatism instead of the parallel plate formed of glass within the scope of the exemplary embodiments of the present invention. However, the present exemplary embodiment is advantageous in view of light amount and cost, similarly to the above-described example.

Figure 7:
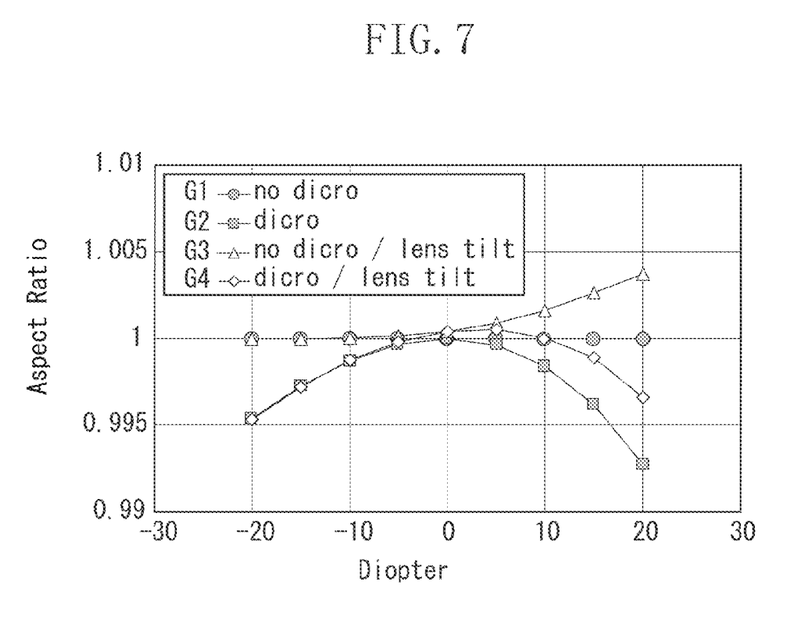
FIG. 7 illustrates an astigmatism correction effect according to an exemplary embodiment of the present invention.

The effect of the above-described correction method will be described in quantitative terms. FIG. 7 illustrates the result of optical calculation performed in the eye refractive power optical system according to the present exemplary embodiment. Optical design software CODE V (manufactured by Optical Research Associates) is used as the calculation tool. The thickness and tilt angle of the dichroic mirror 206 are respectively 3 mm and 45 degrees, and the tilt angle of the objective lens 205 is 2 degrees. Measurement objects are model eyes which do not have an astigmatism component, and a wide range of model eyes from far-sighted to short-sighted are verified.

Referring to FIG. 7, the horizontal axis indicates the spherical refractive power of the model eyes (unit:diopter). The vertical axis indicates a percentage of the ratio between the long and short radiuses of a detected elliptical ring image (i.e., aspect ratio of the ellipse with the width as the denominator). The optical system has a better optical characteristic as the value of the aspect ratio becomes closer to 1 (100%). The elliptical shape becomes more notable as the aspect ratio becomes larger or smaller than 1. The following four conditions are used to set the optical system.

Condition G1: There is no dichroic mirror 206, and the objective lens 205 is arranged to be perpendicular.
Condition G2: The dichroic mirror 206 is included, and the objective lens 205 is arranged to be perpendicular.
Condition G3: There is no dichroic mirror 206, and the objective lens 205 is tilted.
Condition G4: The dichroic mirror 206 is included, and the objective lens 205 is tilted.

In condition G1, the aspect ratio is near 100% regardless of diopter. This indicates that there is no influence of astigmatism. In condition 2, the aspect ratio becomes smaller than 100% with higher positive and negative diopters. This indicates that an astigmatism component is generated due to the influence of the dichroic mirror 206. In condition G3, the aspect ratio becomes larger than 100% with higher positive diopters. This indicates that an astigmatism component is generated due to the influence of the tilted objective lens 205.

When the aspect ratios in conditions G2 and G3 are compared, it is notable that the aspect ratios are inversely related especially with high positive diopters. In condition G4, the aspect ratio becomes smaller than 100% with higher positive and negative diopters, similarly to condition G2.

However, when compared to condition G2, the aspect ratio is closer to 100% especially with higher positive diopters, indicating that an astigmatism component is reduced. The above result quantitatively proves that combining the dichroic mirror 206 and the tilted objective lens 205 allows the astigmatism components generated in the optical system of the apparatus to cancel each other, thereby improving the measurement accuracy of the apparatus.

Figure 8A:
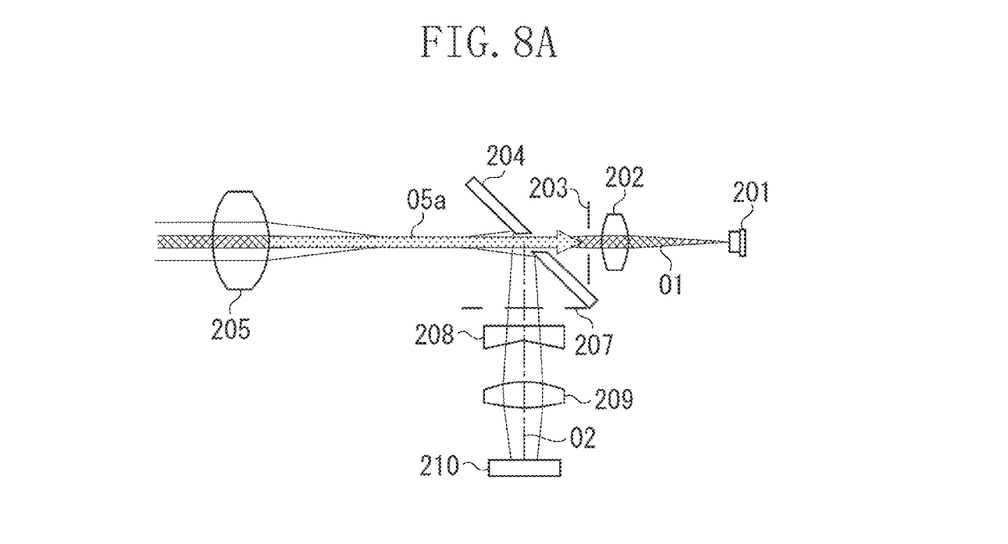
FIGS. 8A and 8B respectively illustrate surface reflected light not appearing as a ghost when the objective lens is not tilted, and surface reflected light appearing as a ghost when the objective lens is tilted.
Figure 8B:
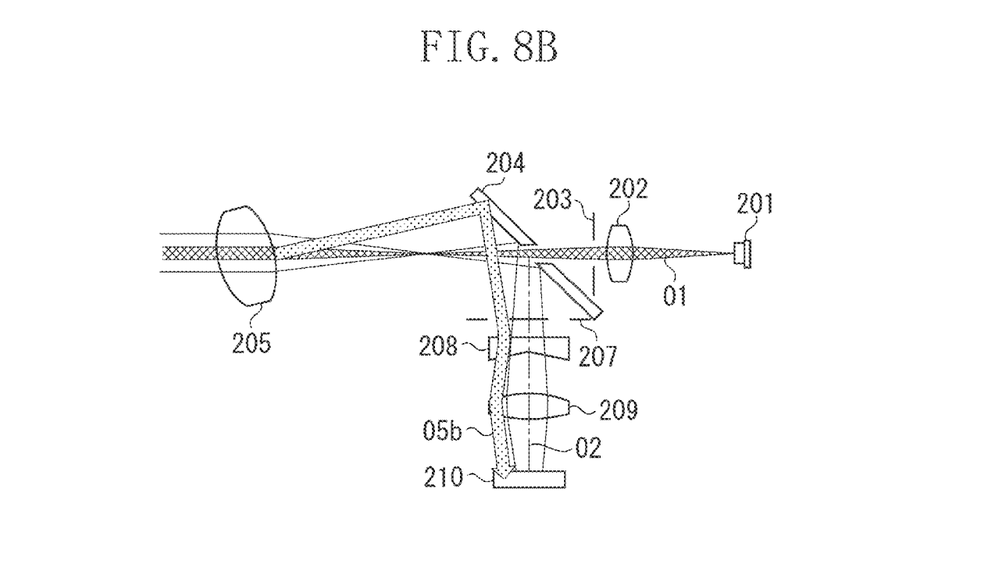

However, simply tilting the objective lens may affect the optical system. FIGS. 8A and 8B illustrate an optical system of the eye refractive power measuring apparatus where the projection light flux 01 heading for a subject's eye is reflected by the surface of the objective lens 205 and then travels towards a light receiving optical system. The light receiving optical system includes the perforated mirror 204, the diaphragm 207, the light flux splitting prism 208, the lens 209, and the image sensor 210. FIG. 8A illustrates the case where the objective lens 205 is perpendicularly arranged as in a conventional manner. FIG. 8B illustrates the case where the objective lens 205 is arranged at a tilt.

In FIG. 8A, the objective lens 205 is arranged perpendicular to the optical axis of the projection light flux 01. A surface reflected light flux 05a from the objective lens 205 thus passes through the perforated portion of the perforated mirror 204 and travels towards the diaphragm 203 along the optical axis of the projection light flux 01. In such a case, the surface reflected light flux 05a is not reflected by the perforated mirror 204 and does not travel towards the light receiving optical system. The surface reflected light flux 05a thus does not appear as an unnecessary ghost.

On the other hand, in FIG. 8B, the objective lens 205 is tilted with respect to the optical axis of the projection light flux 01. The surface reflected light flux 05b from the objective lens 205 thus travels towards the reflective surface of the peripheral portion of the perforated mirror 204 instead of the perforated portion at the center. The surface reflected light flux 05b then passes through the diaphragm 207 and reaches the light receiving surface of the image sensor 210. In such a case, the surface reflected light flux 05b affects the luminance of a detected ring image of the subject's eye by a severe ghost on the ring image. As a result, the surface reflected light flux 05b severely affects the measurement accuracy of the optical system.

Figure 9:
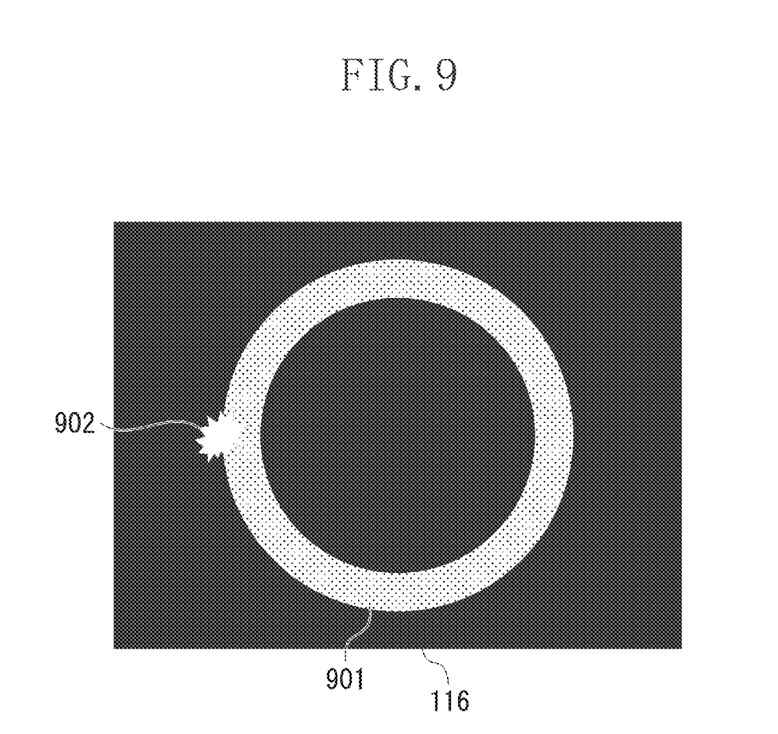
FIG. 9 illustrates surface reflected light appearing as a ghost and entering a ring image when the objective lens is tilted.

FIG. 9 illustrates an example of a detected ring image displayed on the LCD monitor 116 in the case illustrated in FIG. 8B. In FIG. 9, a ghost image 902 is formed on a desired ring image 901. In such a case, an error occurs in a measurement calculation process, so that measurement cannot be performed.

Figure 10:
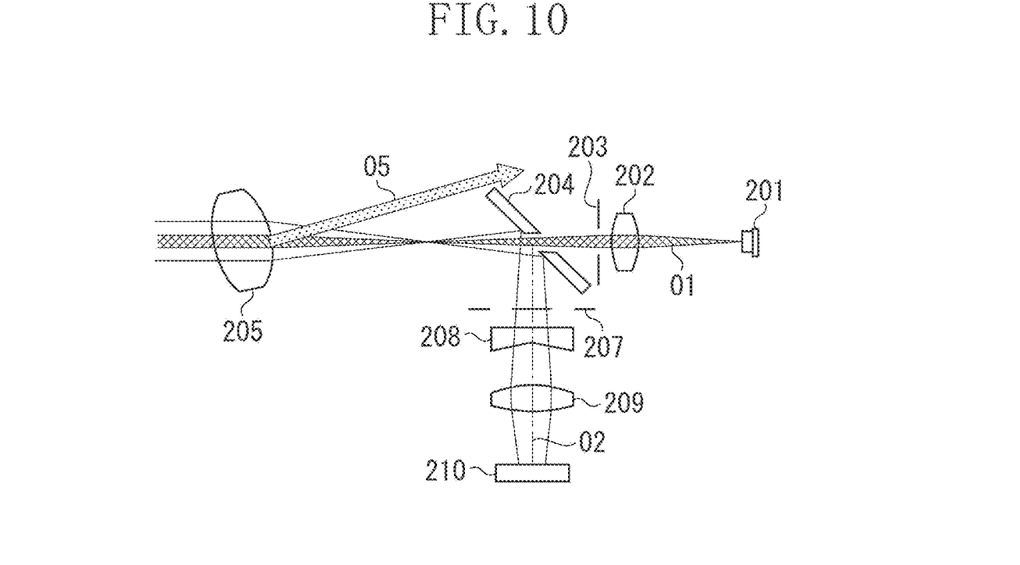
FIG. 10 illustrates an arrangement of a light receiving optical system according to a first exemplary embodiment of the present invention, which prevents surface reflected light from appearing as a ghost when the objective lens is tilted.

As described above, if the objective lens 205 is to be tilted, the light receiving optical system needs to be properly arranged to prevent the formation of a ghost. FIG. 10 illustrates such an example. In FIG. 10, an outer diameter shape of the perforated mirror 204 is determined so that the reflective surface of the perforated mirror 204 does not enter the optical path of the reflected light flux 05 calculated from the tilt of the objective lens 205. In such a case, an effective reflective surface is sufficiently provided for a desired reflected light flux from the subject's eye. As a result, the reflected light flux 05 does not enter the light receiving optical system, so that the measurement can be correctly performed.

According to the present exemplary embodiment, the astigmatism generated by a beam splitting member in a light receiving system can be reduced at low cost and by employing a simple configuration. It can be prevented that generation of astigmatism causes a distorted state of a detected ring image to change, resulting in especially affecting a measurement result of astigmatic refractive power and making it difficult to measure astigmatic refractive power with sufficient accuracy.

Figure 11:
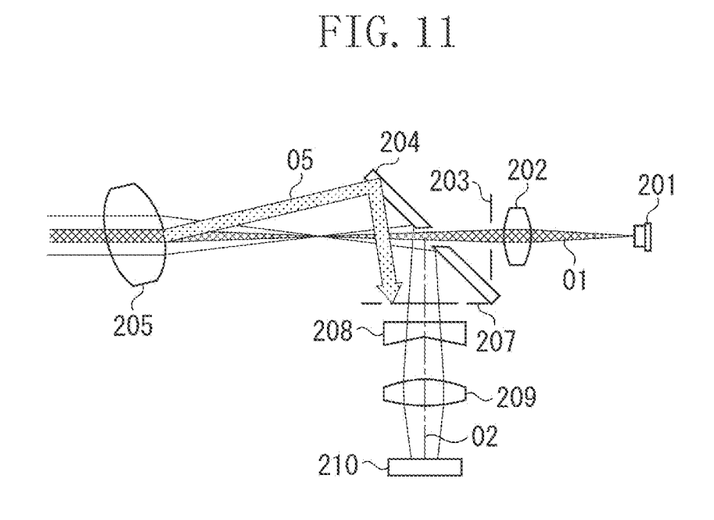
FIG. 11 illustrates an arrangement of a light receiving optical system according to a second exemplary embodiment of the present invention, which prevents surface reflected light from appearing as a ghost when the objective lens is tilted.

Another arrangement example for avoiding appearance of a ghost according to a second exemplary embodiment of the present invention will be described below. Since the description leading to tilting of the objective lens 205 is similar to that of the first exemplary embodiment, such description will be omitted. According to the present exemplary embodiment, the arrangement of the light receiving optical system is different from that in the first exemplary embodiment. FIG. 11 illustrates the configuration of the light receiving optical system according to the present exemplary embodiment. In FIG. 11, the outer diameter shape of the perforated mirror 204 is the same as that in the first exemplary embodiment. However, the shape of the diaphragm 207 has been changed. The surface reflected light flux 05, i.e., the projection light flux 01 reflected by the objective lens 205, is reflected by the reflective surface at the peripheral portion of the perforated mirror 204 and then travels towards the diaphragm 207.

According to the present exemplary embodiment, an inner diameter of the diaphragm 207 is determined so that the optical path of the reflected light flux 05 calculated based on the tilt of the objective lens 205 is blocked by the inner side of the diaphragm 207. In such a case, since the outer diameter of the diaphragm 207 does not change, a pupil diameter to be measured is not affected. There is a concern that the narrowed ring-shaped slit may cause a detected ring image to be thin, and the luminance to be reduced. However, such a concern may be addressed by adjusting the light amount of the measurement light source 201 and/or adjusting gain of the image sensor 210. There is thus hardly any influence on a measurement function of the apparatus. An effect of the present exemplary embodiment can be achieved by the above-described configuration.

According to a third exemplary embodiment of the present invention, a toric lens is used as the objective lens. Since the description other than that of the objective lens 205 and the configuration of the light receiving optical system is the same as that in the first and the second exemplary embodiments, such description will be omitted. According to the above-described exemplary embodiments, the objective lens 205 includes an optical characteristic which reduces the astigmatism generated by a beam splitting member. More specifically, the objective lens 205, which has a rotationally symmetric shape, is arranged as a tilted eccentric lens in the optical system of the eye refractive power measuring apparatus. According to the present exemplary embodiment, the lens has a toric shape in which the curvature radius is different between the X-Z plane and the Y-Z plane, and is arranged to be perpendicular with respect to the optical system of the apparatus as in a conventional manner.

According to the present exemplary embodiment, the reflected light flux 05 from the lens passes through the perforated portion of the perforated mirror 204. Thus considering formation of a ghost is not necessary, and the configuration of the light receiving optical system can be arbitrary. When the lens is toric-shaped, the power is strong in the X-Z plane and weak in the Y-Z plane. As a result, a toric lens itself causes astigmatism to be generated. However, a combination of the astigmatism generated by the lens and the astigmatism generated by the dichroic mirror has an astigmatism correction effect, similarly to the above-described exemplary embodiment, so that the astigmatism in the overall optical system of the apparatus is reduced. An appropriate measurement result can thus be obtained.

Other exemplary embodiments will be described below. According to an exemplary embodiment of the present invention, an ophthalmologic control method to obtain unique information of a subject's eye or alignment information based on an output from an imaging unit includes projecting a light flux on a predetermined region of the subject's eye using a projection optical system, and forming an image of the light flux on an imaging unit using an image-forming optical system. More specifically, the image-forming optical system includes at least one optical element having an optical characteristic which reduces the astigmatism generated by a beam splitting member for forming a split optical path, and is disposed in the optical path between the objective lens facing the subject's eye and the subject's eye.

Further, according to an exemplary embodiment of the present invention, an ophthalmologic control program causes the following process to be executed. Software (program) for realizing the functions of the above-described exemplary embodiments is supplied via a network or various storage media to a system or an apparatus. A computer (or a central processing unit (CPU) or a micro-processing unit (MPU)) in the system or the apparatus reads and executes the program.

Modification Example 1

According to the above-described exemplary embodiments, an objective lens compensates the astigmatism generated by a beam splitting member. However, the present invention is not limited thereto. The lens other than the objective lens in the image-forming optical system, which images, on the image sensor, reflected light from a predetermined region of a subject's eye, may perform compensation of the astigmatism. Further, a combination of the objective lens and an optical element such as the lens other than the objective lens in the image-forming optical system, which images, on the image sensor, reflected light from a predetermined region of a subject's eye may perform compensation of the astigmatism. Furthermore, a combination of the optical elements such as the lens other than the objective lens may perform compensation of the astigmatism.

Modification Example 2

According to the above-described exemplary embodiments, an eye refractive power measuring apparatus is described as the ophthalmologic apparatus. However, the present invention is not limited thereto. The ophthalmologic apparatus may be a fundus camera for imaging a fundus image, an ophthalmologic apparatus which scans and images a subject's eye, and obtains a fundus tomographic image using optical coherence of near-infrared laser beams (i.e., an ophthalmologic optical coherence tomography (OCT) apparatus), or a laser scan ophthalmoscope which obtains a fundus image using confocus (i.e., an ophthalmologic scanning laser ophthalmoscope (SLO)). Moreover, the ophthalmologic apparatus may be a blood flow meter which measures a blood flow amount of blood vessels in a fundus, or a corneal shape measurement apparatus which projects an index light flux on a cornea as a predetermined region of a subject's eye and measures the shape of the cornea.

Modification Example 3

According to the above-described exemplary embodiments, eye refractive power information is obtained as unique information on a subject's eye by projecting an index light flux on a fundus as a predetermined region of a subject's eye and then imaging a light flux from the fundus using an imagine unit via an image-forming optical system. However, the present invention is not limited to obtaining unique information on a subject's eye. For example, alignment information on a subject's eye may be obtained by projecting a parallel light flux on a cornea of a subject's eye, and imaging a light flux reflected from the cornea (i.e., a dispersed light flux from the cornea reflection image as a virtual image formed at the focus position of the cornea) using an imaging unit via an image-forming optical system.

In such a case, an observation optical system, which observes an anterior eye portion of a subject's eye, or a fixed target projection optical system, which fixes a line-of-sight of a subject's eye, is disposed in an optical path split by a dichroic mirror used as a beam splitting member, or by a half mirror (in which a transmission-reflection ratio is not limited to 1:1, and may be an arbitrary value).

Modification Example 4

According to the above-described exemplary embodiments, both a projection optical system for projecting a light flux on a subject's eye, and an image-forming optical system including an objective lens which receives a light flux from a subject's eye via a beam splitting member, include an optical element having an optical characteristic that reduces astigmatism generated by the beam splitting member. However, the present invention is not limited thereto.

Only an image-forming optical system including an objective lens which receives a light flux from a subject's eye via a beam splitting member may include an optical element having an optical characteristic that reduces astigmatism generated by the beam splitting member.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-231020 filed Oct. 18, 2012, which is hereby incorporated by reference herein in its entirety.

What is claimed is:

1. An ophthalmologic apparatus comprising:
a projection optical system configured to project a light flux on a fundus of a subject's eye;
a beam splitting member configured to form a split optical path corresponding to a light flux from the fundus of the subject's eye; and
an image-forming optical system configured to receive a light flux from the fundus of the subject's eye via the beam splitting member, and to form an image of the light flux on an imaging unit;
an optical element having an optical characteristic that reduces astigmatism generated by the beam splitting member; and
an obtaining unit configured to obtain refractive power information of the subject's eye based on an output ring-shaped image from the imaging unit.

2. The ophthalmologic apparatus according to claim 1, wherein the projection optical system includes another optical element different from the optical element, which has an optical characteristic that reduces the astigmatism.

3. The ophthalmologic apparatus according to claim 1, wherein the beam splitting member is a dichroic mirror.

4. The ophthalmologic apparatus according to claim 1, wherein at least one of a fixation target projection optical system, an observation optical system for observing an anterior eye portion of the subject's eye, and an alignment optical system for detecting an alignment state of the subject's eye is disposed in the split optical path.

5. The ophthalmologic apparatus according to claim 1, further comprising:

an objective lens arranged to face the subject's eye,
wherein the beam splitting member is disposed in an optical path between the objective lens and the subject's eye, and
wherein the image-forming optical system is configured to form an image of a light flux from the fundus of the subject's eye via the objective lens and the beam splitting member on the imaging unit.

6. The ophthalmologic apparatus according to claim 5, wherein the projection optical system includes another optical element different from the optical element, which has an optical characteristic that reduces the astigmatism.

7. The ophthalmologic apparatus according to claim 5, wherein the optical element is the objective lens.

8. The ophthalmologic apparatus according to claim 7, wherein the objective lens is tilted in a direction in which astigmatism generated by the beam splitting member is reduced.

9. The ophthalmologic apparatus according to claim 7, wherein the objective lens is a toric lens which reduces astigmatism generated by the beam splitting member.

10. The ophthalmologic apparatus according to claim 5, further comprising a unit configured to prevent surface reflected light by the objective lens from reaching the imaging unit.

11. The ophthalmologic apparatus according to claim 5, wherein the beam splitting member is a dichroic mirror.

12. The ophthalmologic apparatus according to claim 5, wherein at least one of a fixation target projection optical system, an observation optical system for observing an anterior eye portion of the subject's eye, and an alignment optical system for detecting an alignment state of the subject's eye is disposed in the split optical path.

13. The ophthalmologic apparatus according to claim 1, wherein the image-forming optical system includes a ring-shaped diaphragm.

14. An ophthalmologic apparatus comprising:
an optical path splitting member configured to split an optical path;
an optical member configured to be arranged in a tilted state where astigmatism caused by the optical path splitting member can be reduced;
an illumination unit configured to illuminate a subject's eye; and
a detection unit configured to detect a light flux from the subject's eye via the optical path splitting member and the optical member.

15. The ophthalmologic apparatus according to claim 14, wherein the optical member is an objective lens and is arranged to be tilted in a direction different from a direction in which the optical path splitting member is tilted.

16. The ophthalmologic apparatus according to claim 14, wherein the optical member is an objective lens and is arranged on a transmission optical path of the optical path splitting member.

17. A control method for controlling an ophthalmologic apparatus having an optical path splitting member, an optical member, an illumination unit and a detection unit, the control method comprising:
arranging the optical path splitting member to split an optical path;
disposing the optical member in a tilted state where astigmatism caused by the optical path splitting member can be reduced;
illuminating, using the illumination unit, a subject's eye; and
detecting, using the detection unit, a light flux from the subject's eye via the optical path splitting member and the optical member.

18. The control method according to claim 17, wherein the optical member is an objective lens, and
wherein disposing the optical member includes disposing the objective lens to be tilted in a direction different from a direction in which the optical path splitting member is tilted.

19. The control method according to claim 17, wherein the optical member is an objective lens, and
wherein disposing the optical member includes disposing the objective lens on a transmission optical path of the optical path splitting member.

20. A non-transitory computer-readable medium storing a program for causing a computer to execute the control method according to claim 17.

* * * * *